(12) United States Patent
Taira et al.

(10) Patent No.: US 9,304,139 B2
(45) Date of Patent: Apr. 5, 2016

(54) METHOD OF ANALYZING HEMOGLOBINS

(71) Applicant: SEKISUI MEDICAL CO., LTD., Tokyo (JP)

(72) Inventors: Hiroaki Taira, Ibaraki (JP); Takayuki Oka, Ibaraki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/508,143

(22) Filed: Oct. 7, 2014

(65) Prior Publication Data
US 2015/0024503 A1  Jan. 22, 2015

Related U.S. Application Data

(63) Continuation of application No. 13/635,969, filed as application No. PCT/JP2011/056816 on Mar. 22, 2011.

(30) Foreign Application Priority Data

Mar. 31, 2010 (JP) ................. 2010-083726

(51) Int. Cl.
*G01N 33/72* (2006.01)
*G01N 33/48* (2006.01)
*G01N 30/06* (2006.01)
*G01N 30/34* (2006.01)
*G01N 30/88* (2006.01)
*B01D 15/36* (2006.01)
*G01N 30/96* (2006.01)

(52) U.S. Cl.
CPC .............. *G01N 33/721* (2013.01); *G01N 30/06* (2013.01); *G01N 30/34* (2013.01); *B01D 15/362* (2013.01); *G01N 30/96* (2013.01); *G01N 2030/067* (2013.01); *G01N 2030/8822* (2013.01); *G01N 2030/8831* (2013.01); *G01N 2440/00* (2013.01)

(58) Field of Classification Search
CPC . G01N 33/72; G01N 33/721; G01N 2030/06; G01N 2030/067; G01N 2030/8813; G01N 2030/8822; G01N 2030/8831; G01N 30/02; G01N 30/06; G01N 30/88; G01N 30/34; G01N 30/96; B01D 15/362

USPC .............. 436/63, 66, 67, 106, 110, 161, 174, 436/176; 422/70; 210/656, 660, 662, 198.2
See application file for complete search history.

(56) References Cited

U.S. PATENT DOCUMENTS

| | | | |
|---|---|---|---|
| 4,108,603 A | 8/1978 | Regnier et al. | |
| 4,260,516 A | 4/1981 | Moore | |
| 4,438,204 A | 3/1984 | Deeg et al. | |
| 5,223,219 A | 6/1993 | Subaramanian et al. | |
| 6,184,228 B1 | 2/2001 | Corin et al. | |
| 6,428,704 B1 | 8/2002 | Setoguchi et al. | |

FOREIGN PATENT DOCUMENTS

| | | |
|---|---|---|
| EP | 0 077 515 | 4/1983 |
| EP | 0 315 864 | 5/1989 |
| EP | 1 103 812 | 5/2001 |
| JP | S55-162060 | 12/1980 |
| JP | 56-44851 | 4/1981 |
| JP | 58-079163 | 5/1983 |
| JP | 11-166932 | 6/1999 |
| JP | 2003-014714 | 1/2003 |
| JP | 2003-194825 | 7/2003 |
| JP | 2009-97956 | 5/2009 |
| WO | 02/21142 | 3/2002 |

OTHER PUBLICATIONS

International Search Report issued Jun. 14, 2011 in International (PCT) Application No. PCT/JP2011/056816.
Extended European Search Report issued Jan. 7, 2015 in corresponding European Application No. 11765385.7.
Akira Shimizu et al., "Effect of Hemogloblin Variants on Routine HbA1C measurements Assessed by a Mass Spectrometric Method", *The Journal of Japan Society for Clinical Laboratory Automation*, 2000, vol. 25, No. 5, pp. 629-635 (with concise explanation).
Shinji Ogino et al., TOSOH Automated Glycohemoglobin Analyzer HLC-723G9 no kaihatsu (Development of TOSOH Automated Glycohemoglobin Analyzer HLC-723G9), *TOSOH & Technology review*, 2010, vol. 54, pp. 51-55 (with partial translation).

*Primary Examiner* — Maureen Wallenhorst
(74) *Attorney, Agent, or Firm* — Wenderoth, Lind & Ponack, L.L.P.

(57) ABSTRACT

An object of the present invention is to provide a method for analyzing hemoglobins which can accurately separate hemoglobins in a short time by liquid chromatography. The method for analyzing hemoglobins by liquid chromatography includes pretreating a sample with an oxidant and a binder for trivalent heme iron.

7 Claims, 13 Drawing Sheets (a)

(b)

(a)

(b)

(a)

(b)

(a)

(b)

(a)

(b)

(a)

(b)

(a)

(b)

(a)

(b)

(a)

(b)

(a)

(b)

(a)

(b)

(a)

(b)

METHOD OF ANALYZING HEMOGLOBINS

TECHNICAL FIELD

The present invention relates to a method for analyzing hemoglobins by separating hemoglobins by liquid chromatography.

BACKGROUND ART

High-performance liquid chromatography (HPLC) analysis of hemoglobins is a widely used technique. Specifically, this technique is used, for example, to quantify a glycohemoglobin known as hemoglobin A1c or to analyze abnormal hemoglobins for diagnosis of diabetes. For example, a method utilizing liquid chromatography has been known which separates hemoglobin components in a diluted hemolyzed blood sample by a cation-exchange method based on the difference in positive charge among the hemoglobin components. A recent increase in patients with diabetes has also increased the number of cases requiring measurement of hemoglobin A1c. This tendency has created a demand for more accurate, less time-consuming measurement by HPLC.

Hemoglobins are present in the body in the forms of oxyhemoglobin that contains bound oxygen, deoxyhemoglobin that contains bound carbon dioxide, and methemoglobin in which the iron in the heme group is oxidized into the trivalent ion state. In the case of cation-exchange HPLC, oxyhemoglobin, deoxyhemoglobin, and methemoglobin may differ from one another in retention in a separation column and therefore may differ from one another in elution time as well. Consequently, the analysis may provide poor separation accuracy (e.g. detection of broad elution peaks or elution peaks in a bimodal distribution). Moreover, it is known that in the presence of an azide or cyanide, methemoglobin is converted to stable azide methemoglobin or cyanomethemoglobin (hereinafter, also referred to as stable methemoglobin) as a result of binding of the azide or cyanide to the trivalent iron ion in methemoglobin. Since the retention in a separation column is also slightly different among the stable methemoglobin, oxyhemoglobin, and deoxyhemoglobin forms, the presence of stable methemoglobin may cause a broad elution peak or an elution peak in a bimodal distribution to be detected.

HPLC analysis of hemoglobins is mainly used for diagnosis of hemoglobinopathy and thalassemia which may cause anemia, in addition to diabetes. Especially, the number of cases requiring separation and detection of hemoglobin S is large because hemoglobin S is the most common abnormal hemoglobin and causes sickle cell disease which results in severe anemia. On the other hand, in the case of measurement of the diabetes marker hemoglobin A1c, it is preferred to separate abnormal hemoglobins including hemoglobin S in sharp elution peaks. If hemoglobins are eluted in broad elution peaks or elution peaks in a bimodal distribution, separation of the abnormal hemoglobins from normal hemoglobins is difficult and this difficulty may cause a negative impact on obtained measurements.

Furthermore, deteriorated blood samples tend to give broad elution peaks or elution peaks in a bimodal distribution compared to fresh blood samples. This is because the amount of methemoglobin is increased due to deterioration. Therefore, in the case of analysis of a preserved sample (e.g. re-examination), there is a possibility of a negative impact on obtained measurements.

Addition of known antimicrobial agents or saccharides has been known as a technique to prevent hemoglobins from deteriorating and denaturing. Other ways to achieve it are, for example, coexistence of hemoglobins with albumin (Patent Literature 1); coexistence of hemoglobins with casein, boric acid, or the like (Patent Literature 2); and coexistence of hemoglobins with iminocarboxylic acid or a salt thereof (Patent Literature 3).

However, no matter which technique is used among the techniques of Patent Literatures 1 to 3, HPLC measurement of a blood sample containing hemoglobins in various forms including oxyhemoglobin, deoxyhemoglobin, and methemoglobin possibly results in broad elution peaks or elution peaks in a bimodal distribution.

Common HPLC instruments are equipped with a degasser for removing gas in eluents. Such a degasser may cause fluctuations in elution times of hemoglobins and have a negative impact on separation of hemoglobins because its gas removing performance is not stable for a while immediately after start-up. Especially, immediately after start-up or when the temperature of an eluent is unstable, the HPLC instruments are likely to cause fluctuations in elution times of hemoglobins and deterioration of quantification accuracy. This extends the time before a first report of analysis for diabetes diagnosis using hemoglobin A1c as a marker although such analysis requires a rapid result. Therefore, there is a need for a technique for providing stable measurement even immediately after start-up of an HPLC instrument.

Generally, absorbance obtained by a spectrophotometei is a measure to detect and quantify hemoglobins. The coexistence of oxyhemoglobin, deoxyhemoglobin, methemoglobin, azidemethemoglobin, and cyanmethemoglobin may inhibit accurate quantification of hemoglobins because of their different absorption spectra.

CITATION LIST

Patent Literature

Patent Literature 1: JP-A 2003-194825
Patent Literature 2: JP-A 11-166932
Patent Literature 3: JP-A 2009-97956

SUMMARY OF INVENTION

Technical Problem

An object of the present invention is to provide a method for analyzing hemoglobins which can accurately separate hemoglobins in a short time by liquid chromatography.

Solution to Problem

The present invention is a method for analyzing hemoglobins by liquid chromatography, comprising pre-treating a sample with an oxidant and a binder for trivalent heme iron.

The following description is offered to describe the present invention in detail.

The present inventors found that pre-treatment on a sample with an oxidant and a binder for trivalent heme iron converts all of hemoglobins in the sample to their stable methemoglobin forms, and therefore eliminates variations in the retention to a fixed phase in a column among forms of each hemoglobin. Thus, the pre-treatment was found to enable hemoglobins to be accurately separated in a short time, and the present invention was completed.

The method for analyzing hemoglobins of the present invention includes pre-treating a sample with an oxidant and a binder for trivalent heme iron.

The pre-treatment with an oxidant and a binder for trivalent heme iron on a sample improves resolution of hemoglobins and reduces elution times of hemoglobins. Additionally, even in the case of using an HPLC instrument equipped with a degasser whose gas removal ability is not stable immediately after start-up, hemoglobins can be accurately separated without showing fluctuations in their elution times or giving broad elution peaks and elution peaks in a bimodal distribution.

In the present invention, the "pre-treatment with an oxidant and a binder for trivalent heme iron on a sample" means a treatment which is performed on the sample using an oxidant and a binder for trivalent heme iron before separation of hemoglobins through a separation column, and is not limited to treatments to be performed before measurement by liquid chromatography. Specifically, a sample can be treated with an oxidant and a binder for trivalent heme iron before separation of hemoglobins, for example, by mixing any one of the combinations shown in Table 1, that is, the oxidant and/or the binder for trivalent heme iron in a sample pre-treatment solution and/or eluent(s). In Table 1, "O" indicates that the corresponding agent was used and "-" indicates that the corresponding agent was not used.

TABLE 1

|   |   | Oxidant | Binder for trivalent heme iron |
|---|---|---|---|
| ① | Sample pre-treatment solution | O | O |
|   | Eluent | O | O |
| ② | Sample pre-treatment solution | O | O |
|   | Eluent | O | — |
| ③ | Sample pre-treatment solution | O | O |
|   | Eluent | — | O |
| ④ | Sample pre-treatment solution | O | O |
|   | Eluent | — | — |
| ⑤ | Sample pre-treatment solution | O | — |
|   | Eluent | O | O |
| ⑥ | Sample pre-treatment solution | — | O |
|   | Eluent | O | O |
| ⑦ | Sample pre-treatment solution | — | — |
|   | Eluent | O | O |
| ⑧ | Sample pre-treatment solution | O | — |
|   | Eluent | — | O |
| ⑨ | Sample pre-treatment solution | — | O |
|   | Eluent | O | — |

In the method for analyzing hemoglobins of the present invention, the oxidant converts heme iron in hemoglobins from the divalent form to the trivalent form, thereby transforming the hemoglobins into their methemoglobin forms.

The oxidant is not particularly limited, provided that it is capable of converting heme iron in hemoglobins from the divalent form to the trivalent form. Examples thereof include nitrites, potassium ferricyanide, methylene blue, hydrogen peroxide, ascorbic acid, and hydrogen sulfide. Particularly, nitrites are preferable, and sodium nitrite and potassium nitrite are more preferable. These oxidants do not decompose hemoglobins because of their not so strong oxidation ability. Additionally, these oxidants prevent large changes in the elution pattern which are caused when an oxidant binds to methemoglobin, and also prevent fluctuations of the base line during HPLC measurement which are caused by interference between the wavelength for hemoglobin detection and the absorption spectrum of an oxidant. Therefore, more precise quantification of hemoglobins is ensured.

In the method for analyzing hemoglobins of the present invention, the binder for trivalent heme iron converts methemoglobin to stable methemoglobin.

Examples of the binder for trivalent heme iron include azides and cyanides. When the binder for trivalent heme iron is an azide or cyanide, it does not alter the structure of methemoglobin so much, and therefore does not change the elution pattern of hemoglobins so much. Accordingly, more precise quantification of hemoglobins is ensured.

Examples of azides include sodium azide, diphenylphosphoryl azide, 4-dodecylbenzenesulfonyl azide, 4-acetylamidobenzenesulfonyl azide, potassium azide, lithium azide, iron azide, hydrogen azide, lead azide, mercury azide, copper azide, and silver azide.

Examples of cyanides include potassium cyanide, hydrogen cyanide, sodium cyanide, silver cyanide, mercury cyanide, copper cyanide, lead cyanide, iron cyanide, lithium cyanide, and ammonium cyanide.

Among these binders for trivalent heme iron, sodium azide is preferable.

Examples of the sample pre-treatment solution include organic acids and salts thereof, amino acids, inorganic acids and salts thereof, and known buffers containing a buffering agent such as a Good's buffer.

Examples of organic acids include citric acid, succinic acid, tartaric acid, and malic acid.

Examples of amino acids include glycine, taurine, and arginine.

Examples of inorganic acids include hydrochloric acid, nitric acid, sulfuric acid, phosphoric acid, boric acid, and acetic acid.

The above buffers may optionally contain any of surfactants, various polymers, hydrophilic low-molecular-weight compounds, and the like.

The buffering agent concentration in the sample pre-treatment solution is not particularly limited. The preferable lower limit thereof is 5 mmol/L and the preferable upper limit thereof is 500 mmol/L. If the buffering agent concentration is lower than 5 mmol/L, the buffer action may not be enough. If the buffering agent concentration is higher than 500 mmol/L, the buffering agent may be precipitated to clog a path of the HPLC instrument. The more preferable lower limit of the buffering agent concentration is 10 mmol/L and the more preferable upper limit thereof is 200 mmol/L.

When the sample pre-treatment solution contains the oxidant, the oxidant concentration in the sample pre-treatment solution is not particularly limited. The preferable lower limit thereof is 0.05 mmol/L and the preferable upper limit thereof is 50 mmol/L. If the oxidant concentration in the sample pre-treatment solution is lower than 0.05 mmol/L, a sufficient amount of hemoglobins may not be transformed into the met-forms. In this case, oxyhemoglobin and deoxyhemoglobin may be still present in the sample, which may cause a broad elution peak or an elution peak in a bimodal distribution to be detected. If the oxidant concentration in the sample pre-treatment solution is higher than 50 mmol/L, methemoglobin may be decomposed. In this case, an elution peak thereof may not be detected, or an elution peak may be detected at a different elution time. The more preferable lower limit of the oxidant concentration in the sample pre-treatment solution is 0.5 mmol/L and the more preferable upper limit thereof is 25 mmol/L.

When the sample pre-treatment solution contains the binder for trivalent heme iron, the concentration of the binder for trivalent heme iron in the sample pre-treatment solution is not particularly limited. The preferable lower limit thereof is 0.05 mmol/L and the preferable upper limit thereof is 50 mmol/L. If the concentration of the binder for trivalent heme iron in the sample pre-treatment solution is lower than 0.05 mmol/L, a sufficient amount of the binder may not bind to trivalent heme iron in methemoglobin, which may cause a broad elution peak or an elution peak in a bimodal distribution to be detected. If the concentration of the binder for trivalent heme iron in the sample pre-treatment solution is higher than 50 mmol/L, methemoglobin may be decomposed. In this case, an elution peak thereof may not be detected, or an elution peak may be detected at a different elution time. The more preferable lower limit of the concentration of the binder for trivalent heme iron in the sample pre-treatment solution is 0.5 mmol/L and the more preferable upper limit thereof is 25 mmol/L.

The pH of the sample pre-treatment solution is not particularly limited, but the preferable lower limit thereof is 4.0 and the preferable upper limit thereof is 10.0. If the pH of the sample pre-treatment solution is less than 4.0 or more than 10.0, the stability of hemoglobins is deteriorated. In this case, no elution peak may be detected or an elution peak may be detected at a different elution time. The more preferable lower limit of the pH of the sample pre-treatment solution is 6.0, and the more preferable upper limit thereof is 8.5.

Examples of the eluents include organic acids and salts thereof, amino acids, inorganic acids and salts thereof, and known buffers containing a buffering agent such as a Good's buffer.

Examples of organic acids include citric acid, succinic acid, tartaric acid, and malic acid.

Examples of amino acids include glycine, taurine, and arginine.

Examples of inorganic acids include hydrochloric acid, nitric acid, sulfuric acid, phosphoric acid, boric acid, and acetic acid.

The buffer may optionally contain any of surfactants, various polymers, hydrophilic low-molecular-weight compounds, and the like.

The buffering agent concentration in the eluents is not particularly limited, but the preferable lower limit thereof is 5 mmol/L and the preferable upper limit thereof is 500 mmol/L. If the buffering agent concentration is lower than 5 mmol/L, the buffer action may not be enough. If the buffering agent concentration is higher than 500 mmol/L, the buffering agent may be precipitated to clog a path of the HPLC instrument; or reduce the eluent replacement efficiency, resulting in a longer time for equilibration. The more preferable lower limit of the buffering agent concentration is 10 mmol/L, and the preferable upper limit is 200 mmol/L.

When eluent(s) contain the oxidant, the oxidant concentration in the eluents is not particularly limited. The preferable lower limit thereof is 0.05 mmol/L and the preferable upper limit thereof is 50 mmol/L. If the oxidant concentration in the eluents is lower than 0.05 mmol/L, a sufficient amount of hemoglobins may not be transformed into the met-forms. In this case, oxyhemoglobin and deoxyhemoglobin may be still present in the sample, which may cause a broad elution peak or an elution peak in a bimodal distribution to be detected. The use of an eluent having an oxidant concentration of higher than 50 mmol/L may cause elution at too short times, thereby resulting in poor resolution. It should be noted that the elution times can be controlled by adjusting the concentrations of components such as the buffer agent in the eluents within ranges in which methemoglobin is not decomposed. The more preferable lower limit of the oxidant concentration in the eluents is 0.5 mmol/L, and the more preferable upper limit thereof is 25 mmol/L.

When eluent(s) contain the binder for trivalent heme iron, the concentration of the binder for trivalent heme iron in the eluents is not particularly limited. The preferable lower limit thereof is 0.05 mmol/L and the preferable upper limit thereof is 50 mmol/L. If the concentration of the binder for trivalent heme iron in the eluents is lower than 0.05 mmol/L, a sufficient amount of hemoglobins may not be transformed into the met-forms. In this case, oxyhemoglobin and deoxyhemoglobin may be still present in the sample, which may cause a broad elution peak or an elution peak in a bimodal distribution to be detected. The use of an eluent having a concentration of the binder for trivalent heme iron of higher than 50 mmol/L may cause elution at too short times, thereby resulting in poor resolution. It should be noted that the elution times can be controlled by adjusting the concentrations of components such as the buffer agent in the eluents within ranges in which methemoglobin is not decomposed. The more preferable lower limit of the concentration of the binder for trivalent heme iron in the eluents is 0.5 mmol/L, and the more preferable upper limit thereof is 25 mmol/L.

In the method for analyzing hemoglobins of the present invention, in the case that the oxidant and the binder for trivalent heme iron are mixed only in eluent(s), the oxidant and the binder for trivalent heme iron should be mixed in at least the first eluent to be supplied for HPLC measurement. It is preferable to mix the oxidant and the binder for trivalent heme iron to other eluent(s) in addition to the first eluent to be supplied for HPLC measurement, and is more preferable to mix them in all the eluents used for the measurement.

The eluents may contain a pH adjuster such as a known acid or base. Examples of the acid include hydrochloric acid, phosphoric acid, nitric acid, and sulfuric acid. Examples of the base include sodium hydroxide, potassium hydroxide, lithium hydroxide, magnesium hydroxide, barium hydroxide, and calcium hydroxide.

The eluents may contain a water-soluble organic solvent such as methanol, ethanol, acetonitrile, or acetone. The organic solvent is preferably added at such a concentration that a salt or other components in eluent are not precipitated, and the preferable upper limit of the concentration is 80% (v/v).

The pH of the eluents is not particularly limited, but the preferable lower limit thereof is 4.0 and the preferable upper limit thereof is 10.0. The use of an eluent having a pH of less than 4.0 may cause a broad leading peak, a broad elution peak, or an elution peak in a bimodal distribution to be detected. In the case of an eluent having a pH of more than 10.0, hemoglobins may exhibit low retention in a fixed phase in a column and thus may be eluted at extremely short times. Additionally, such an eluent may cause a broad tailing peak, a broad elution peak, or an elution peak in a bimodal distribution to be detected. By controlling the pH to 4.0 or more and 10.0 or less, it is possible to avoid deterioration of the stability of hemoglobins in a sample under analysis and also avoid detection failure of elution peaks of hemoglobins or detection of an elution peak at a different elution time. The more preferable lower limit of the pH of the eluents is 6.0, and the more preferable upper limit thereof is 8.5.

The liquid chromatography used in the method for analyzing hemoglobins of the present invention is preferably ion-exchange liquid chromatography.

The ion-exchange liquid chromatography may be performed in a known manner, for example, by conveying an eluent by a pump to a separation column, introducing a sample to the eluent after the eluent passes through a degasser on the way to the separation column, separating hemoglobins in the separation column, and detecting the separated components in the eluent released from the column with a detector.

The separation column is a column containing a fixed phase. Examples of the fixed phase include filler particles and porous materials. Particularly, filler particles are preferred.

Examples of the filler particles include inorganic particles and organic particles.

Examples of the inorganic particles include particles made of silica, zirconia, or the like.

Examples of the organic particles include natural polymer particles of cellulose, a polyamino acid, chitosan, or the like, and synthetic polymer particles of polystyrene, a polyacrylic acid ester, or the like.

The fixed phase is preferably a fixed phase that has a cation-exchange group.

Examples of the cation-exchange group include carboxyl, phosphate, and sulfonic acid groups.

The analysis conditions in the method for analyzing hemoglobins of the present invention can be appropriately determined based on samples to be analyzed, the type of the column, and the like. Specifically, the preferable lower limit of the flow rate of the eluents is 0.05 mL/min, and the preferable upper limit thereof is 5 mL/min. The more preferable lower limit is 0.2 mL/min, and the more preferable upper limit is 3 mL/min. The detection wavelength for hemoglobins is preferably, but is not limited only to, 415 nm.

Generally, samples to be analyzed are those prepared by hemolyzing a blood sample with a solution that contains a substance having a hemolytic activity such as a surfactant, and diluting the hemolyzed blood sample. The amount of a sample to be introduced depends on the dilution ratio of the blood sample but is preferably about 0.1 to 100 µL.

Advantageous Effects of Invention

The method for analyzing hemoglobins of the present invention enables short-term analysis with excellent resolution and facilitates separation of hemoglobins which have been hard to separate by conventional techniques.

Thus, the present invention enables hemoglobins to be accurately separated and analyzed in a short time by liquid chromatography.

DESCRIPTION OF EMBODIMENTS

Figure 1:
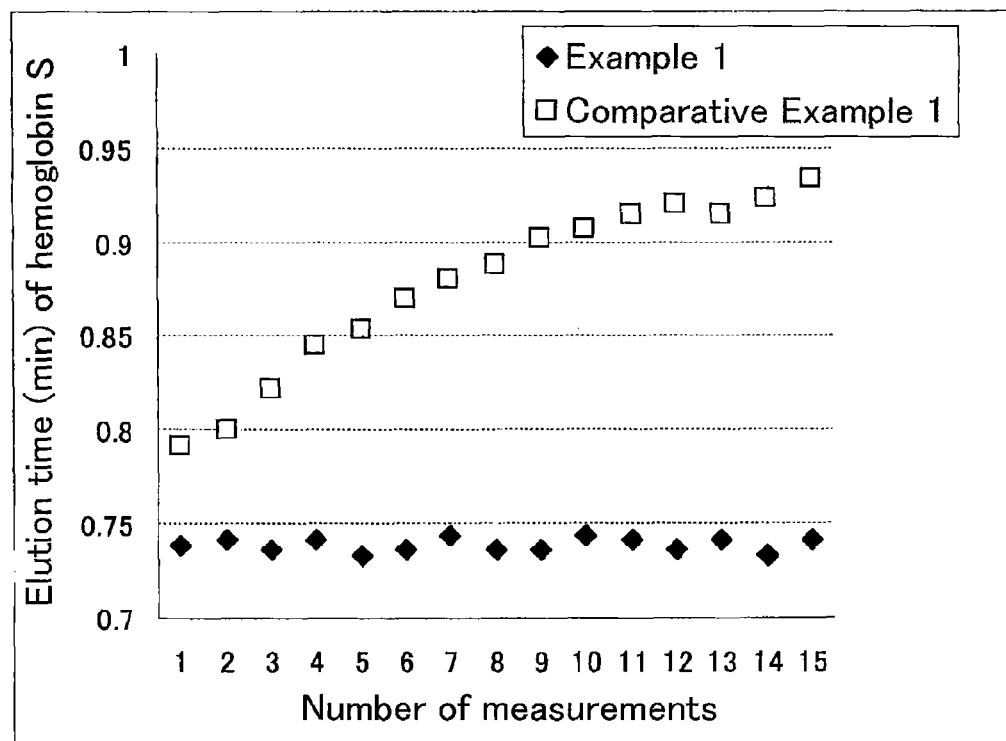
FIG. 1 is a graph showing the relationship between the number of measurements and the elution time of hemoglobin S in Example 1 and Comparative Example 1.

The following description will discuss the present invention in more detail by way of Examples, but the scope of the present invention is not limited only to these examples.

EXAMPLE 1

A sample was prepared by diluting a hemoglobin S-containing blood sample 100-fold with a sample pre-treatment solution (phosphate buffer (pH 7.0) containing 0.1% by weight Triton X-100).

The used separation column was a column containing cation-exchange resin filler particles having sulfonic acid groups on the surfaces.

The used HPLC instrument was provided with an autosampler SIL-20AC (Shimadzu Corp.), a delivery pump LC-20AD (Shimadzu Corp.), a degasser DGU-20A5 (Shimadzu Corp.), a column oven CTO-20AC (Shimadzu Corp.), and a detector SPD-M20A (Shimadzu Corp.). The instrument was run under the following conditions:
  eluent flow rate: 1.7 mL/min;
  detection wavelength: 415 nm; and
  amount of introduced sample: 10 µL.

Each portion of the sample was eluted and measured using the following eluents for the respective periods of time:
  until 0.5 minutes after the start: eluent 1 (40 mmol/L phosphate buffer (pH 5.4) containing 60 mmol/L sodium perchlorate, 1 mmol/L sodium nitrite, and 1 mmol/L sodium azide);
  from 0.5 minutes to 1.0 minute after the start: eluent 2 (20 mmol/L phosphate buffer (pH 7.0) containing 10 mmol/L sodium perchlorate, 1 mmol/L sodium nitrite, and 1 mmol/L sodium azide);
  from 1.0 minute to 1.1 minutes after the start: eluent 3 (40 mmol/L phosphate buffer (pH 8.0) containing 0.8% by weight Triton X-100, 300 mmol/L sodium perchlorate, and 1 mmol/L sodium azide); and
  from 1.1 minutes to 1.5 minutes after the start: eluent 1.

The measurement was continuously repeated 15 times immediately after start-up of the HPLC instrument.

COMPARATIVE EXAMPLE 1

The same sample as that of Example 1 was used.

Each portion of the sample was measured in the same manner as in Example 1, except that eluent 4 (40 mmol/L phosphate buffer (pH 5.4) containing 60 mmol/L sodium perchlorate and 1 mmol/L sodium azide) was used instead of eluent 1 and eluent 5 (20 mmol/L phosphate buffer (pH 7.0) containing 10 mmol/L sodium perchlorate and 1 mmol/L sodium azide) was used instead of eluent 2.

FIG. 1 is a graph showing the relationship between the number of measurements and the elution time of hemoglobin S in Example 1 and Comparative Example 1. As seen in FIG. 1, the elution time of hemoglobin S became longer as the number of measurements increased in Comparative Example 1. On the other hand, the elution time of hemoglobin S was constant regardless of the number of measurements in Example 1.

EXAMPLE 2

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100).

Another sample was prepared by diluting a hemoglobin S-containing blood sample 100-fold with the sample pre-treatment solution (10 mmol/L phosphate buffer (pH 7.0) containing 0.1% by weight Triton X-100).

The same separation column as that of Example 1 was used.

The same HPLC instrument as that of Example 1 was run under the following conditions:
flow rate: 1.7 mL/min;
detection wavelength: 415 nm; and
amount of introduced sample: 10 μL.

Each sample was eluted and measured by linear gradient of two eluents:
first eluent: eluent 6 (20 mmol/L phosphate buffer (pH 5.4) containing 30 mmol/L sodium perchlorate, 1 mmol/L sodium nitrite, and 1 mmol/L sodium azide); and
second eluent: eluent 7 (40 mmol/L phosphate buffer (pH 8.0) containing 0.8% by weight Triton X-100, 300 mmol/L sodium perchlorate, 1 mmol/L sodium nitrite, and 1 mmol/L sodium azide).

Figure 2:
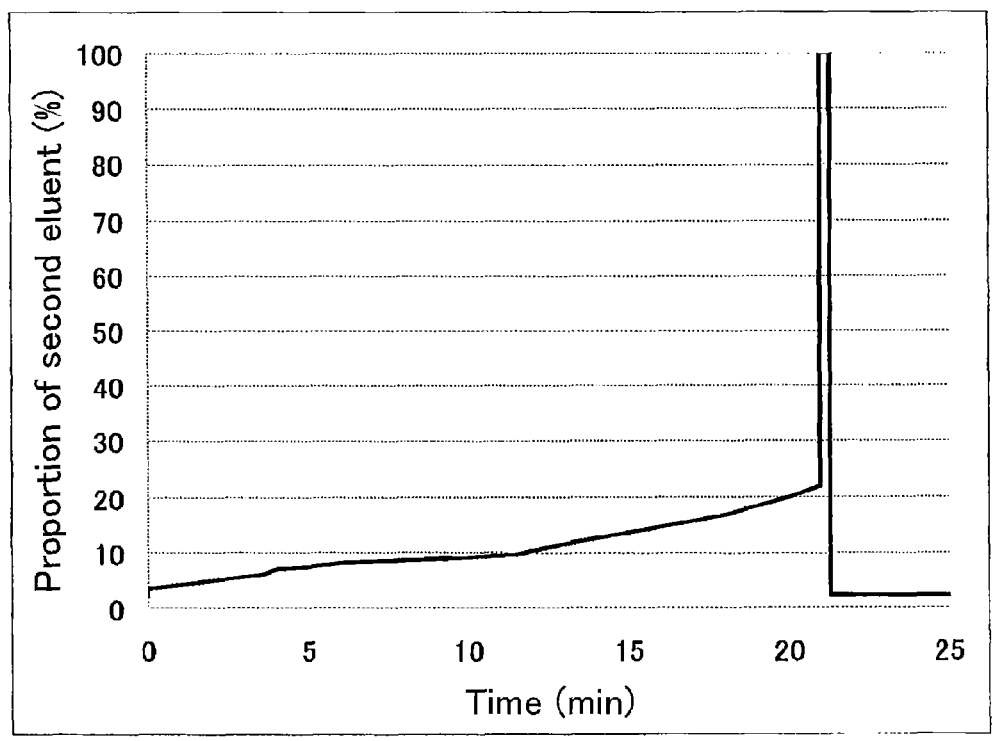
FIG. 2 is a graph showing the gradient of the first eluent and the second eluent in Example 2.
Figure 3:
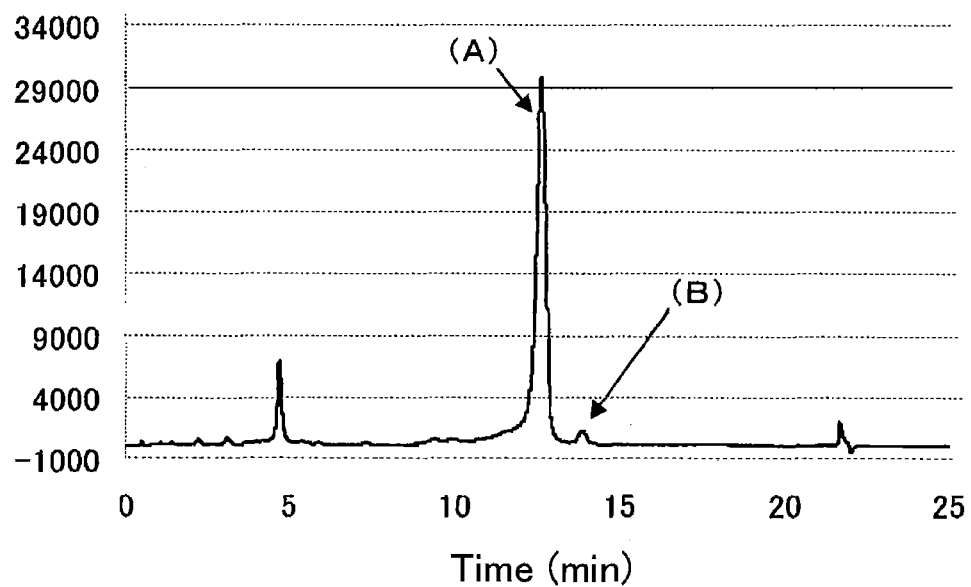
FIGS. 3(a) and 3(b) are chromatograms respectively obtained by measurement of a sample containing glycohemoglobin control level II and a sample containing hemoglobin S-containing blood in Example 2.
Figure 3:
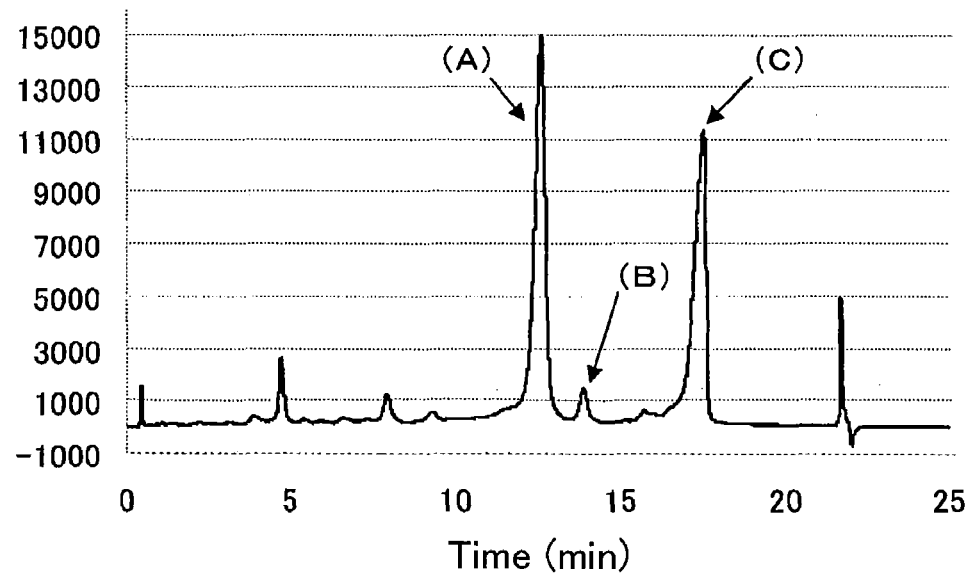

FIG. 2 is a graph showing the gradient of the first eluent and the second eluent in Example 2. FIG. 2 shows the proportion (% by weight) of the second eluent to the total amount of the first eluent and the second eluent. FIG. 3 are the resulting chromatograms.

EXAMPLE 3

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100, 1 mmol/L sodium nitrite, and 1 mmol/L sodium azide).

Another sample was prepared by diluting a hemoglobin S-containing blood sample 100-fold with the sample pre-treatment solution (10 mmol/L phosphate buffer (pH 7.0) containing 0.1% by weight Triton X-100, 1 mmol/L sodium nitrite, and 1 mmol/L sodium azide).

Figure 4:
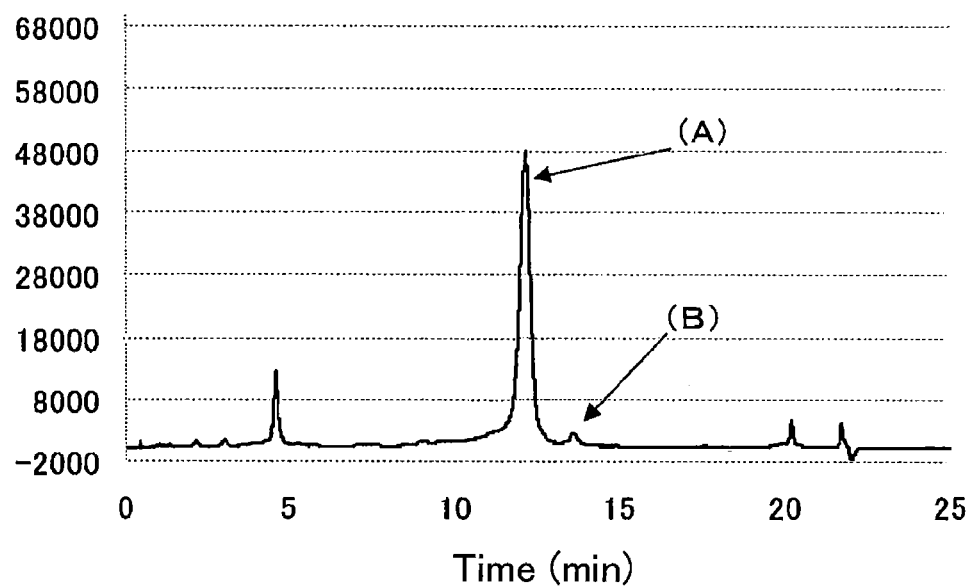
FIGS. 4(a) and 4(b) are chromatograms respectively obtained by measurement of a sample containing glycohemoglobin control level II and a sample containing hemoglobin S-containing blood in Example 3.
Figure 4:
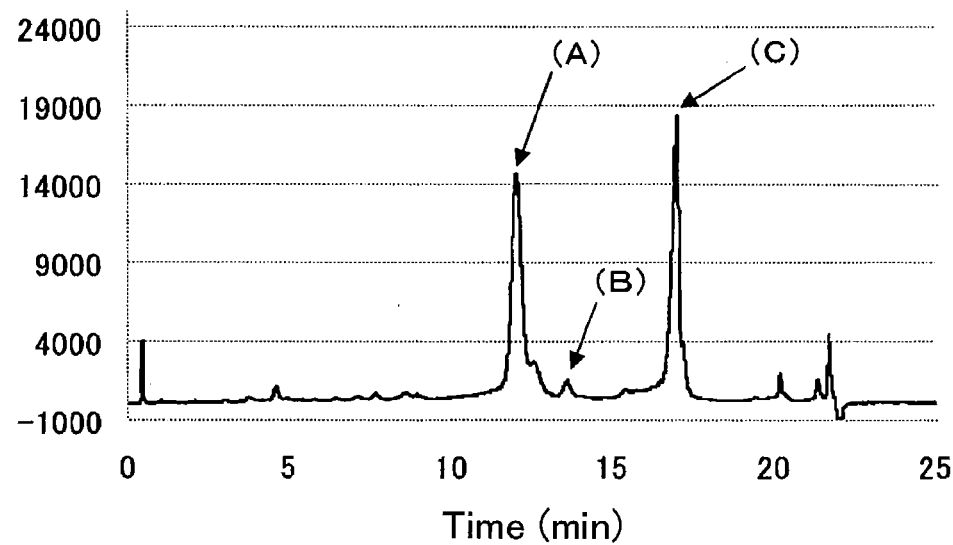

The samples were measured in the same manner as in Example 2, except that eluent 3 (40 mmol/L phosphate buffer (pH 8.0) containing 0.8% by weight Triton X-100, 300 mmol/L sodium perchlorate, and 1 mmol/L sodium azide) used in Example 1 was used as the second eluent. FIG. 4 are the resulting chromatograms.

EXAMPLE 4

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100).

Another sample was prepared by diluting a hemoglobin S-containing blood sample 100-fold with the sample pre-treatment solution (10 mmol/L phosphate buffer (pH 7.0) containing 0.1% by weight Triton X-100).

Figure 5:
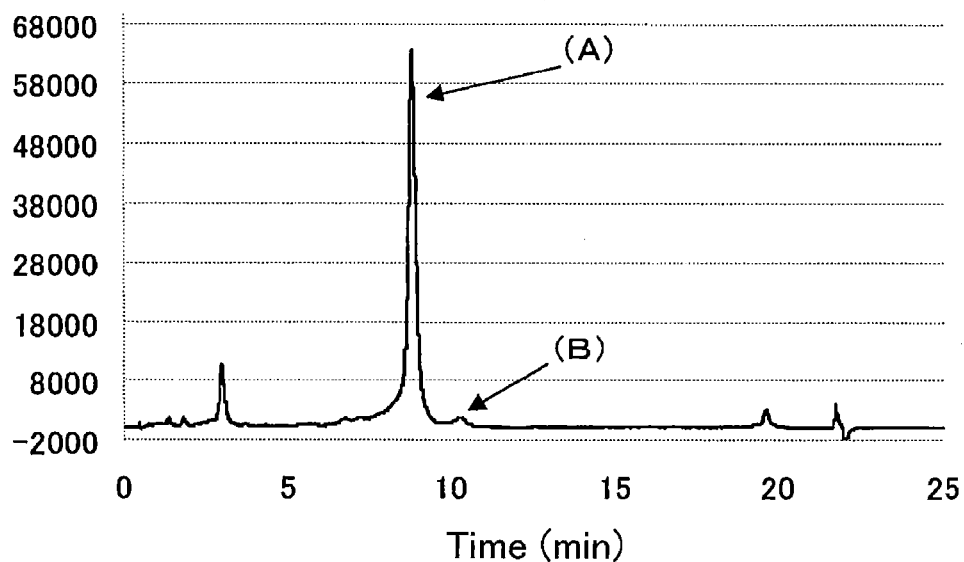
FIGS. 5(a) and 5(b) are chromatograms respectively obtained by measurement of a sample containing glycohemoglobin control level II and a sample containing hemoglobin S-containing blood in Example 4.
Figure 5:
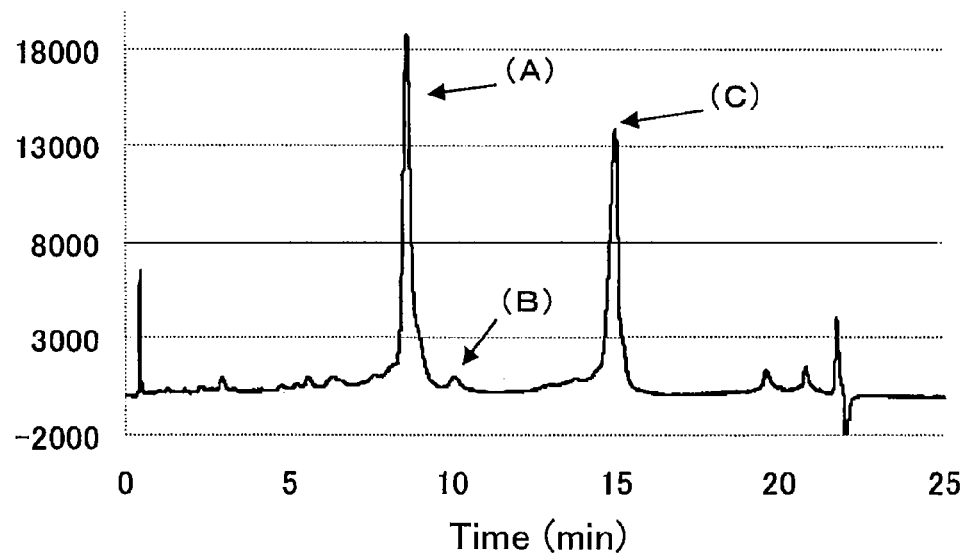

The samples were measured in the same manner as in Example 2, except that eluent 8 (20 mmol/L phosphate buffer (pH 5.4) containing 30 mmol/L sodium perchlorate, 10 mmol/L sodium nitrite, and 1 mmol/L sodium azide) was used as the first eluent, and eluent 9 (40 mmol/L phosphate buffer (pH 8.0) containing 0.8% by weight Triton X-100, 300 mmol/L sodium perchlorate, 10 mmol/L sodium nitrite, and 1 mmol/L sodium azide) was used as the second eluent. FIG. 5 are the resulting chromatograms.

EXAMPLE 5

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100).

Another sample was prepared by diluting a hemoglobin S-containing blood sample 100-fold with the sample pre-treatment solution (10 mmol/L phosphate buffer (pH 7.0) containing 0.1% by weight Triton X-100).

Figure 6:
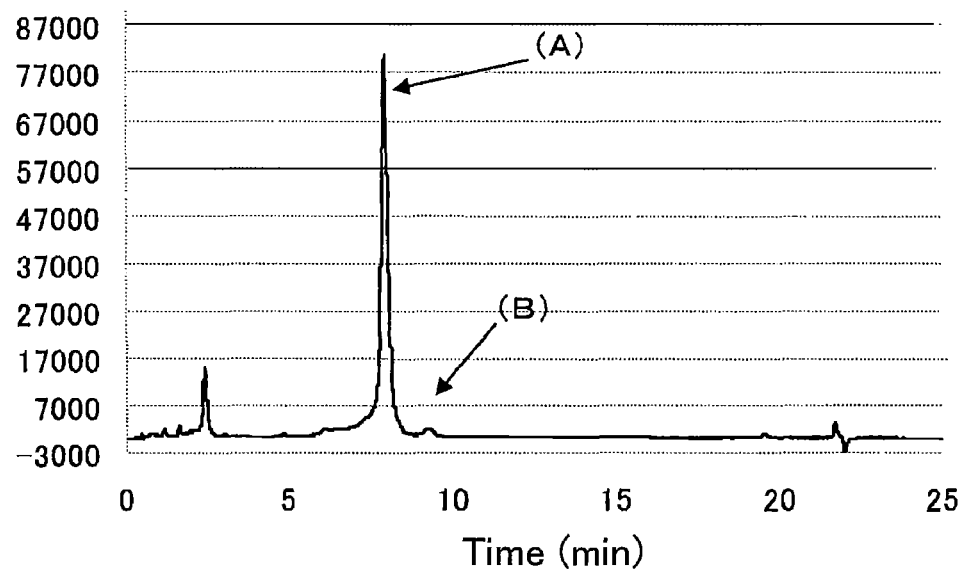
FIGS. 6(a) and 6(b) are chromatograms respectively obtained by measurement of a sample containing glycohemoglobin control level II and a sample containing hemoglobin S-containing blood in Example 5.
Figure 6:
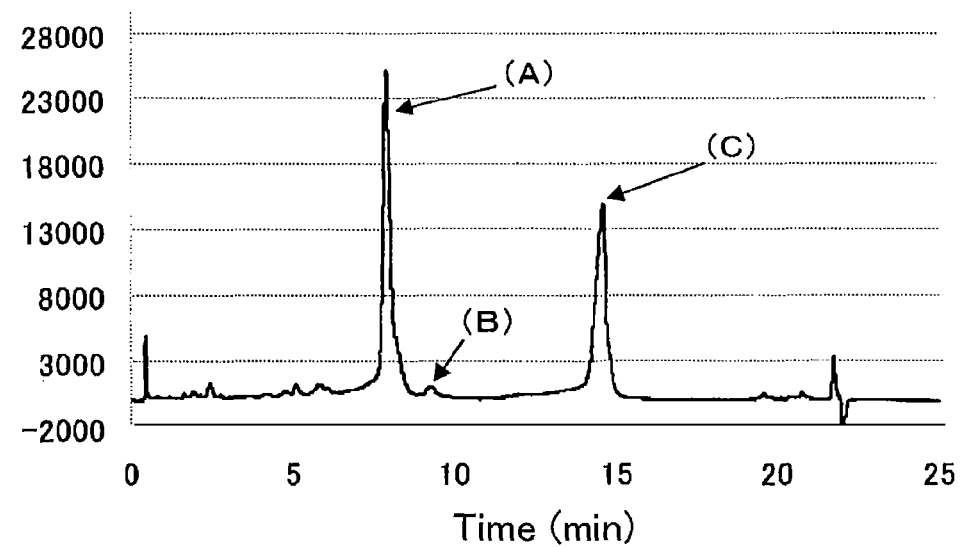

The samples were measured in the same manner as in Example 2, except that eluent 10 (20 mmol/L phosphate buffer (pH 5.4) containing 30 mmol/L sodium perchlorate, 1 mmol/L sodium nitrite, and 10 mmol/L sodium azide) was used as the first eluent, and eluent 11 (40 mmol/L phosphate buffer (pH 8.0) containing 0.8% by weight Triton X-100, 300 mmol/L sodium perchlorate, 1 mmol/L sodium nitrite, and 10 mmol/L sodium azide) was used as the second eluent. FIG. 6 are the resulting chromatograms.

EXAMPLE 6

A sample was prepared by dissolving glycohemoglobin control level II (Sysmex Corp) in water for injection (200 μL), and further diluting the solution 100-fold with a sample pre-treatment solution (10 mmol/L phosphate buffer (pH 7.0) containing 0.1% by weight Triton X-100).

Another sample was prepared by diluting a hemoglobin S-containing blood sample 100-fold with the sample pre-treatment solution (10 mmol/L phosphate buffer (pH 7.0) containing 0.1% by weight Triton X-100).

Figure 7:
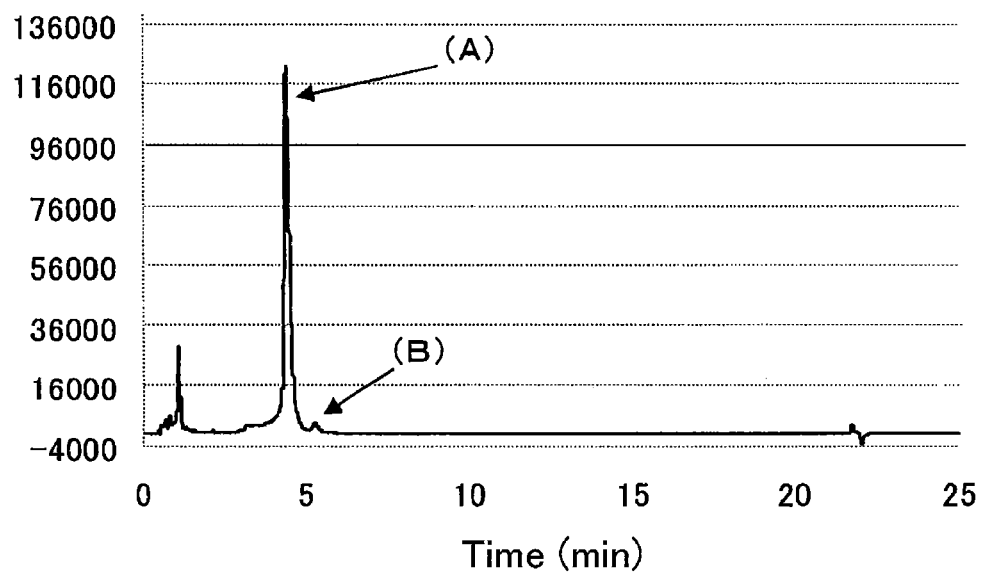
FIGS. 7(a) and 7(b) are chromatograms respectively obtained by measurement of a sample containing glycohemoglobin control level II and a sample containing hemoglobin S-containing blood in Example 6.
Figure 7:
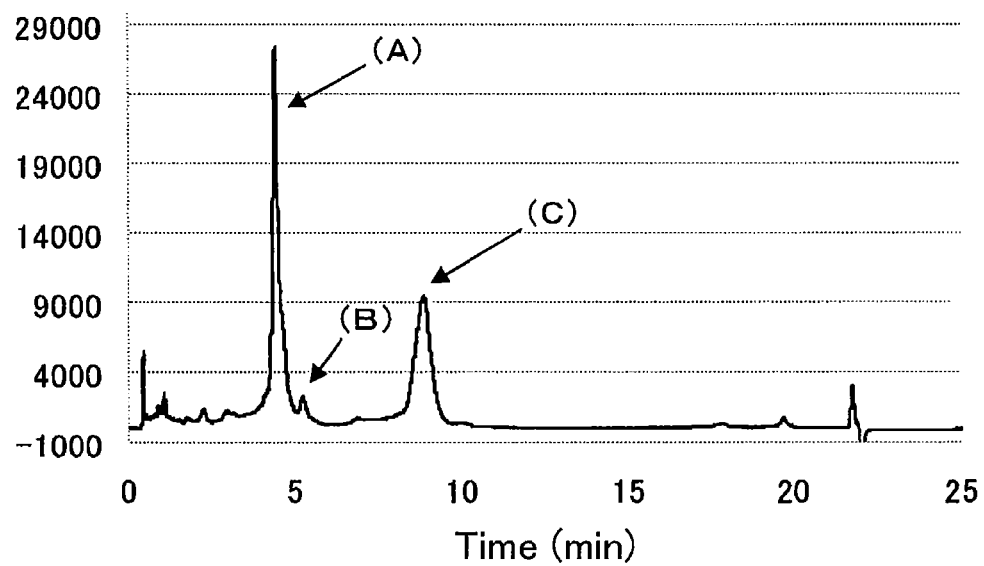

The samples were measured in the same manner as in Example 2, except that eluent 12 (20 mmol/L phosphate buffer (pH 5.4) containing 30 mmol/L sodium perchlorate, 10 mmol/L sodium nitrite, and 10 mmol/L sodium azide) was used as the first eluent, and eluent 13 (40 mmol/L phosphate buffer (pH 8.0) containing 0.8% by weight Triton X-100, 300 mmol/L sodium perchlorate, 10 mmol/L sodium nitrite, and 10 mmol/L sodium azide) was used as the second eluent. FIG. 7 are the resulting chromatograms.

EXAMPLE 7

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100, 1 mmol/L potassium ferricyanide, and 1 mmol/L sodium azide).

Another sample was prepared by diluting a hemoglobin S-containing blood sample 100-fold with the sample pre-treatment solution (10 mmol/L phosphate buffer (pH 7.0) containing 0.1% by weight Triton X-100, 1 mmol/L potassium ferricyanide, and 1 mmol/L sodium azide).

Figure 8:
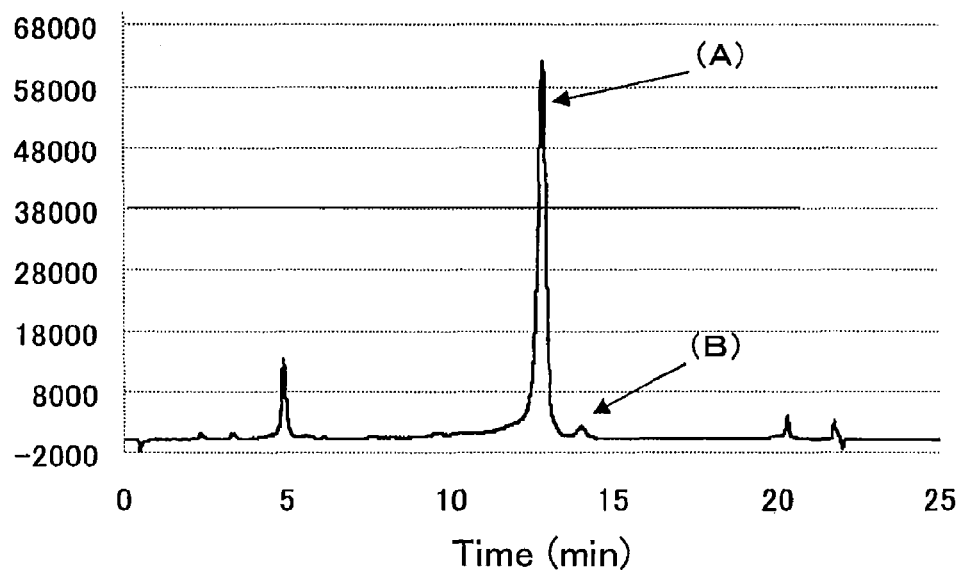
FIGS. 8(a) and 8(b) are chromatograms respectively obtained by measurement of a sample containing glycohemoglobin control level II and a sample containing hemoglobin S-containing blood in Example 7.
Figure 8:
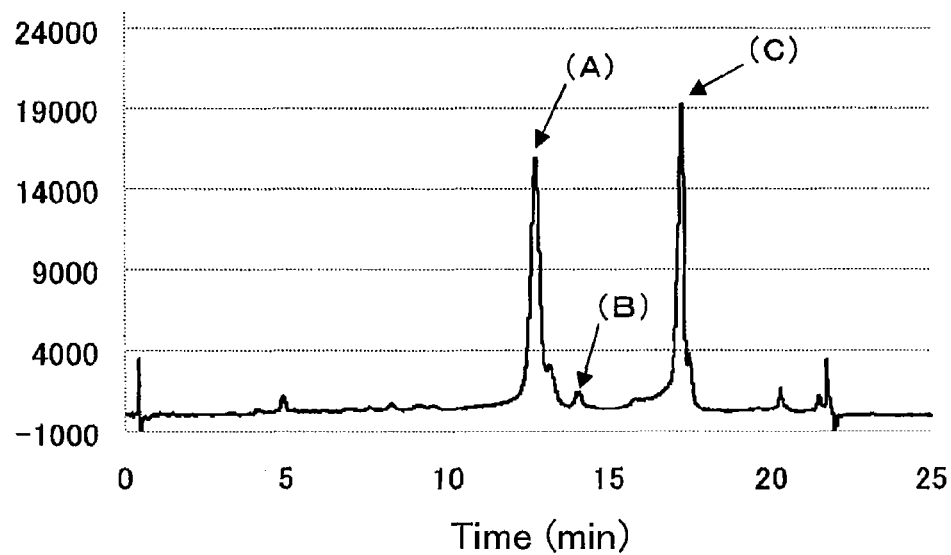

The samples were measured in the same manner as in Example 2, except that eluent 14 (20 mmol/L phosphate buffer (pH 5.4) containing 30 mmol/L sodium perchlorate, 1 mmol/L potassium ferricyanide, and 1 mmol/L sodium azide) was used as the first eluent, and eluent 15 (40 mmol/L phosphate buffer (pH 8.0) containing 0.8% by weight Triton X-100, 300 mmol/L sodium perchlorate, 1 mmol/L potassium ferricyanide, and 1 mmol/L sodium azide) was used as the second eluent. FIG. 8 are the resulting chromatograms.

EXAMPLE 8

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100 and 1 mmol/L sodium azide).

Another sample was prepared by diluting a hemoglobin S-containing blood sample 100-fold with the sample pre-treatment solution (10 mmol/L phosphate buffer (pH 7.0) containing 0.1% by weight Triton X-100 and 1 mmol/L sodium azide).

Figure 9:
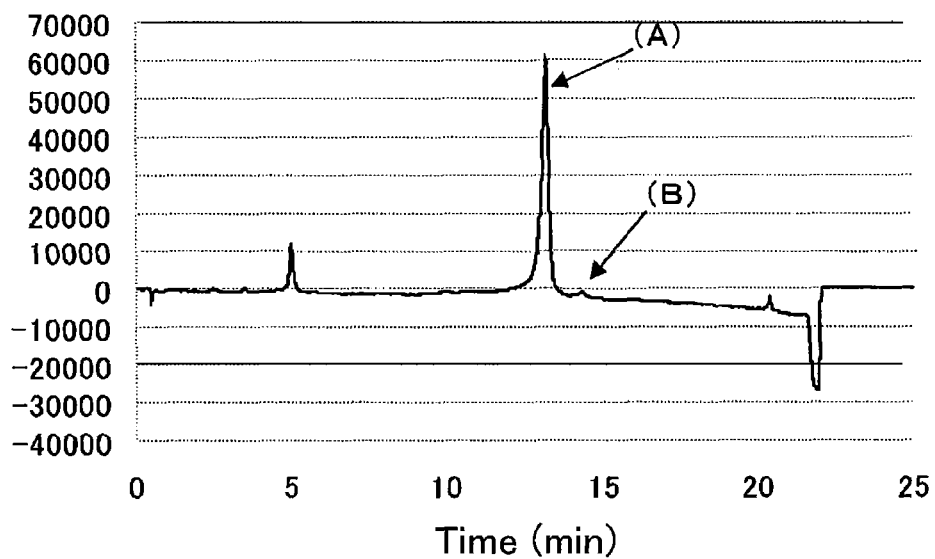
FIGS. 9(a) and 9(b) are chromatograms respectively obtained by measurement of a sample containing glycohemoglobin control level II and a sample containing hemoglobin S-containing blood in Example 8.
Figure 9:
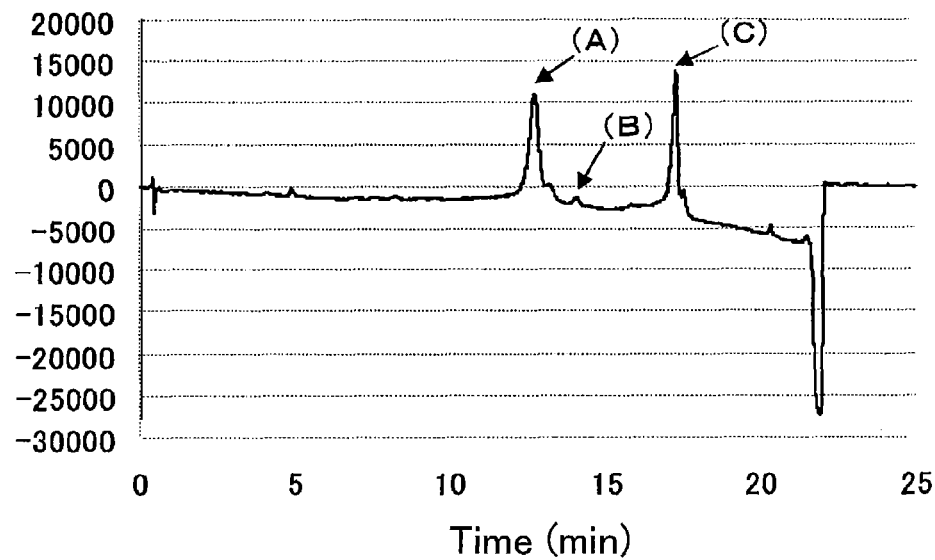

The samples were measured in the same manner as in Example 2, except that eluent 16 (20 mmol/L phosphate buffer (pH 5.4) containing 30 mmol/L sodium perchlorate, 1 mmol/L sodium ferricyanide, and 1 mmol/L sodium azide) was used as the first eluent, and eluent 3 (40 mmol/L phosphate buffer (pH 8.0) containing 0.8% by weight Triton X-100, 300 mmol/L sodium perchlorate, and 1 mmol/L sodium azide) used in Example 1 was used as the second eluent. FIG. 9 are the resulting chromatograms.

COMPARATIVE EXAMPLE 2

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100 and 1 mmol/L sodium azide).

Another sample was prepared by diluting a hemoglobin S-containing blood sample 100-fold with the sample pre-treatment solution (10 mmol/L phosphate buffer (pH 7.0) containing 0.1% by weight Triton X-100 and 1 mmol/L sodium azide).

Figure 10:
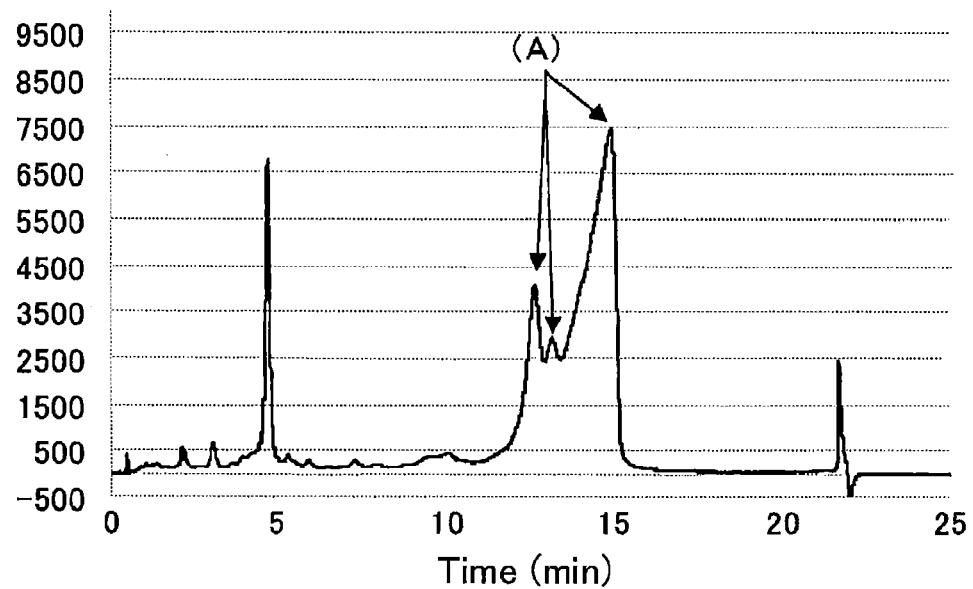
FIGS. 10(a) and 10(b) are chromatograms respectively obtained by measurement of a sample containing glycohemoglobin control level II and a sample containing hemoglobin S-containing blood in Comparative Example 2.
Figure 10:
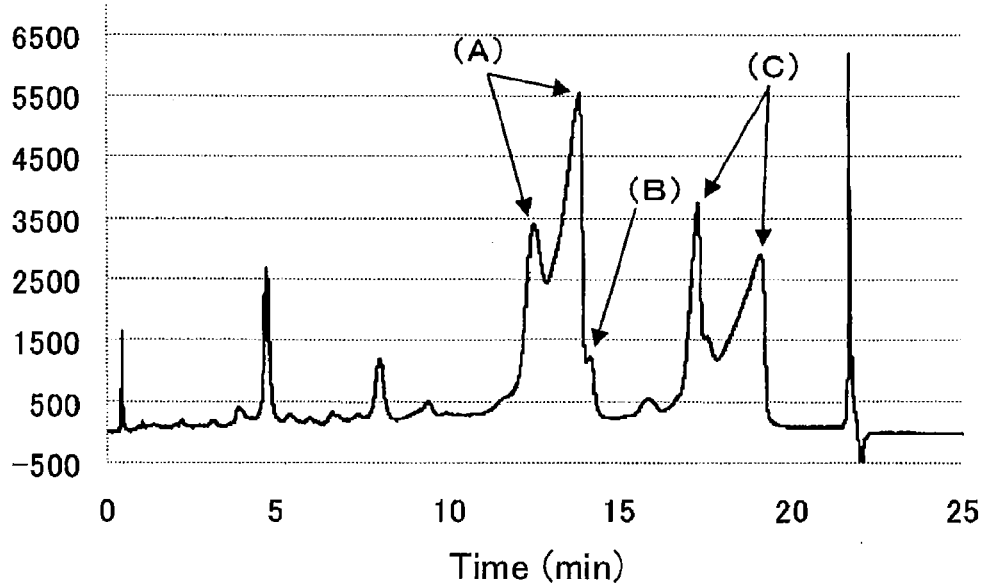

The samples were measured in the same manner as in Example 2, except that eluent 17 (20 mmol/L phosphate buffer (pH 5.4) containing 30 mmol/L sodium perchlorate and 1 mmol/L sodium azide) was used as the first eluent, and eluent 3 (40 mmol/L phosphate buffer (pH 8.0) containing 0.8% by weight Triton X-100, 300 mmol/L sodium perchlorate, and 1 mmol/L sodium azide) used in Example 1 was used as the second eluent. FIG. 10 are the resulting chromatograms.

COMPARATIVE EXAMPLE 3

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100 and 1 mmol/L sodium nitrite).

Another sample was prepared by diluting a hemoglobin S-containing blood sample 100-fold with the sample pre-treatment solution (10 mmol/L phosphate buffer (pH 7.0) containing 0.1% by weight Triton X-100 and 1 mmol/L sodium nitrite).

Figure 11:
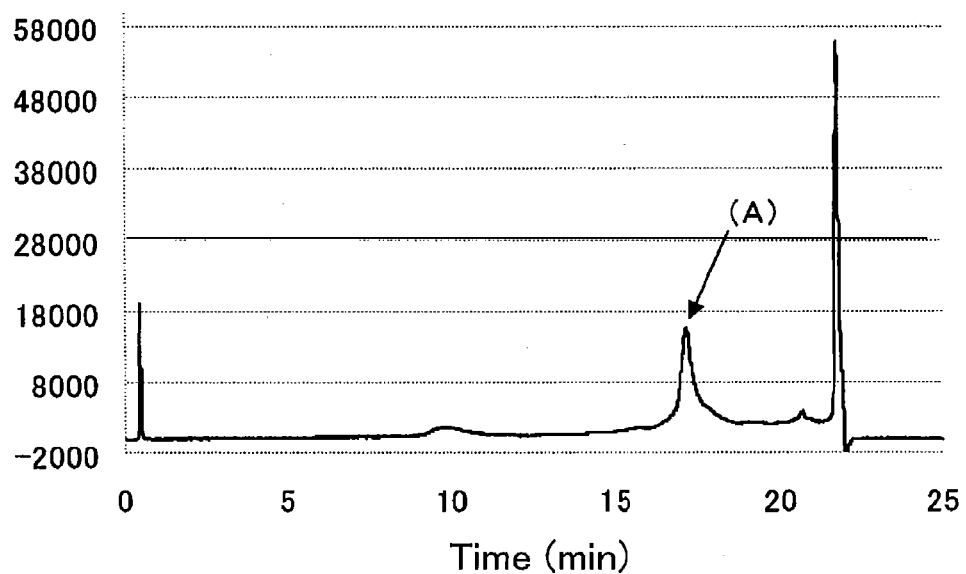
FIGS. 11(a) and 11(b) are chromatograms respectively obtained by measurement of a sample containing glycohemoglobin control level II and a sample containing hemoglobin S-containing blood in Comparative Example 3.
Figure 11:
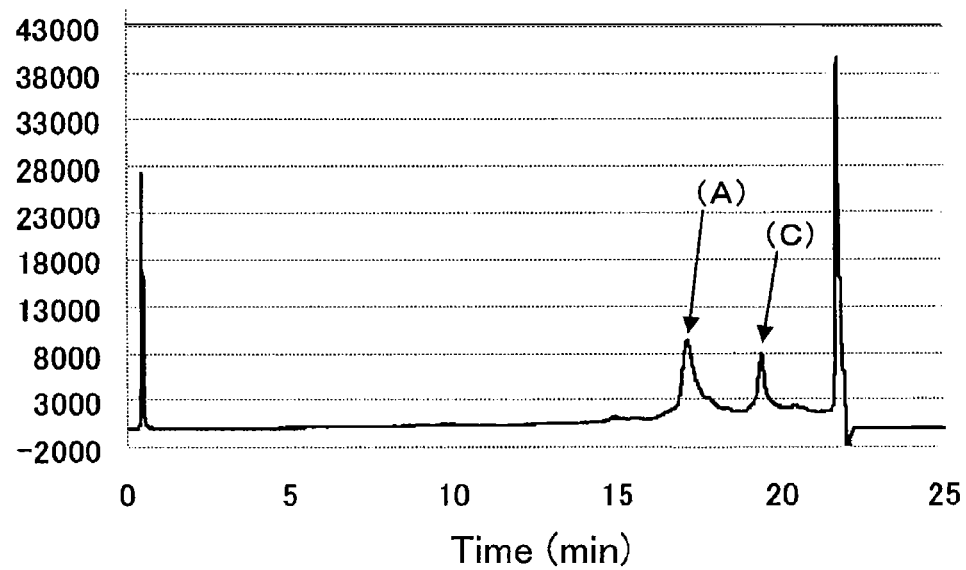

The samples were measured in the same manner as in Example 2, except that eluent 18 (20 mmol/L phosphate buffer (pH 5.4) containing 30 mmol/L sodium perchlorate and 1 mmol/L sodium nitrite) was used as the first eluent, and eluent 19 (40 mmol/L phosphate buffer (pH 8.0) containing 0.8% by weight Triton X-100, 300 mmol/L sodium perchlorate, and 1 mmol/L sodium nitrite) was used as the second eluent. FIG. 11 are the resulting chromatograms.

COMPARATIVE EXAMPLE 4

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100).

Another sample was prepared by diluting a hemoglobin S-containing blood sample 100-fold with the sample pre-treatment solution (10 mmol/L phosphate buffer (pH 7.0) containing 0.1% by weight Triton X-100).

Figure 12:
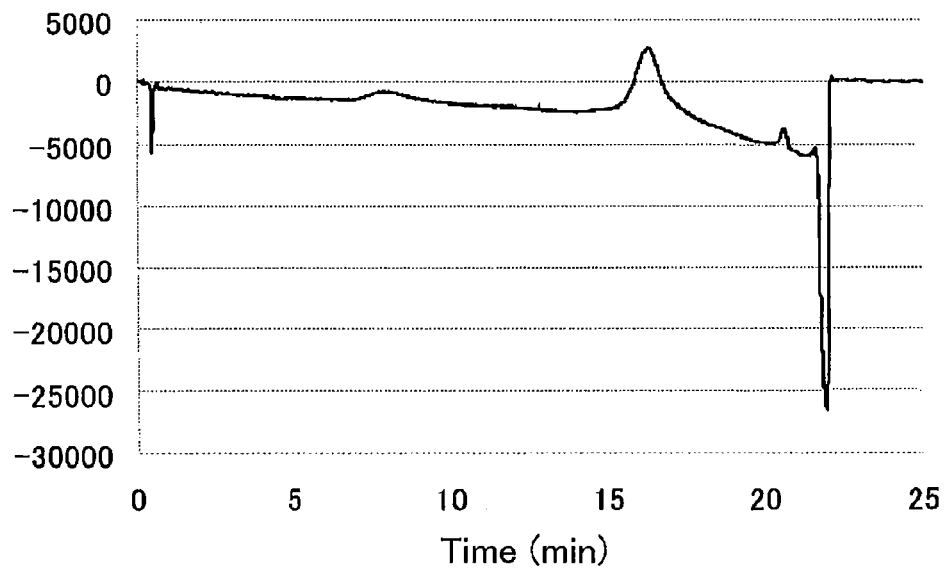
FIGS. 12(a) and 12(b) are chromatograms respectively obtained by measurement of a sample containing glycohemoglobin control level II and a sample containing hemoglobin S-containing blood in Comparative Example 4.
Figure 12:
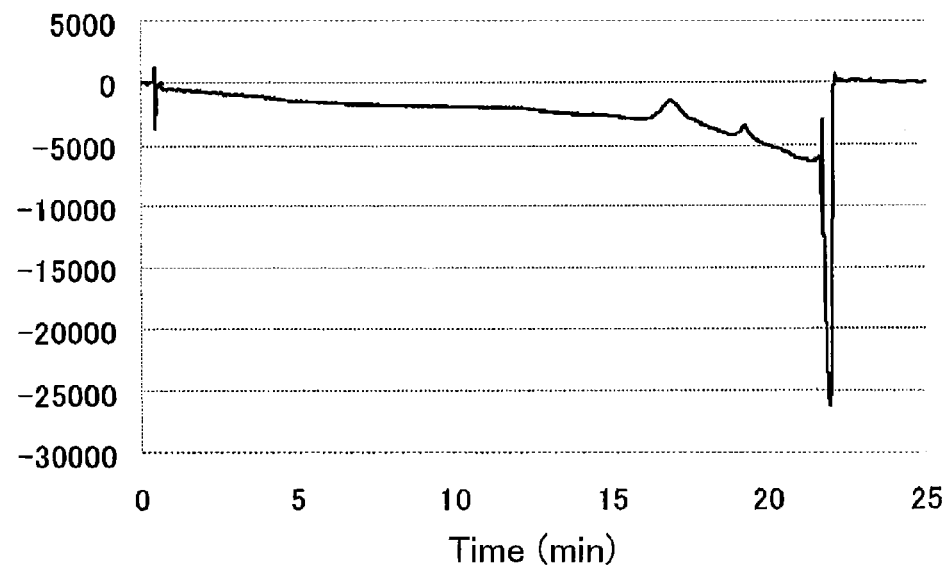

The samples were measured in the same manner as in Example 2, except that eluent 20 (20 mmol/L phosphate buffer (pH 5.4) containing 30 mmol/L sodium perchlorate and 1 mmol/L potassium ferricyanide) was used as the first eluent, and eluent 21 (40 mmol/L phosphate buffer (pH 8.0) containing 0.8% by weight Triton X-100 and 300 mmol/L sodium perchlorate) was used as the second eluent. FIG. 12 are the resulting chromatograms.

EXAMPLE 9

A sample was prepared by dissolving glycohemoglobin control level II (Sysmex Corp.) was dissolved in water for injection (200 μL), and further diluting the solution 100-fold with a sample pre-treatment solution (10 mmol/L phosphate buffer (pH 7.0) containing 0.1% by weight Triton X-100).

Another sample was prepared by diluting a hemoglobin S-containing blood sample 100-fold with the sample pre-treatment solution (10 mmol/L phosphate buffer (pH 7.0) containing 0.1% by weight Triton X-100).

Figure 13:
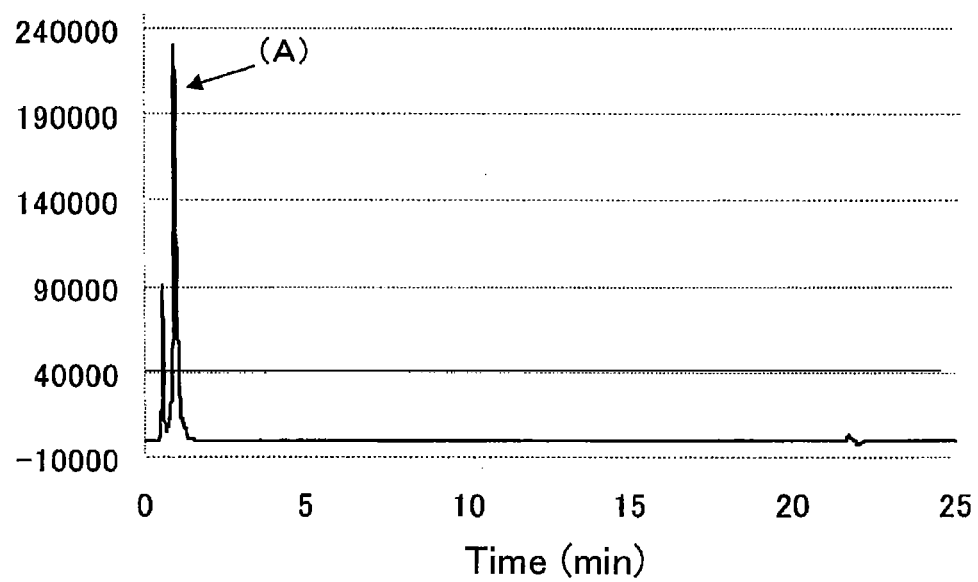
FIGS. 13(a) and 13(b) are chromatograms respectively obtained by measurement of a sample containing glycohemoglobin control level II and a sample containing hemoglobin S-containing blood in Example 9.
Figure 13:
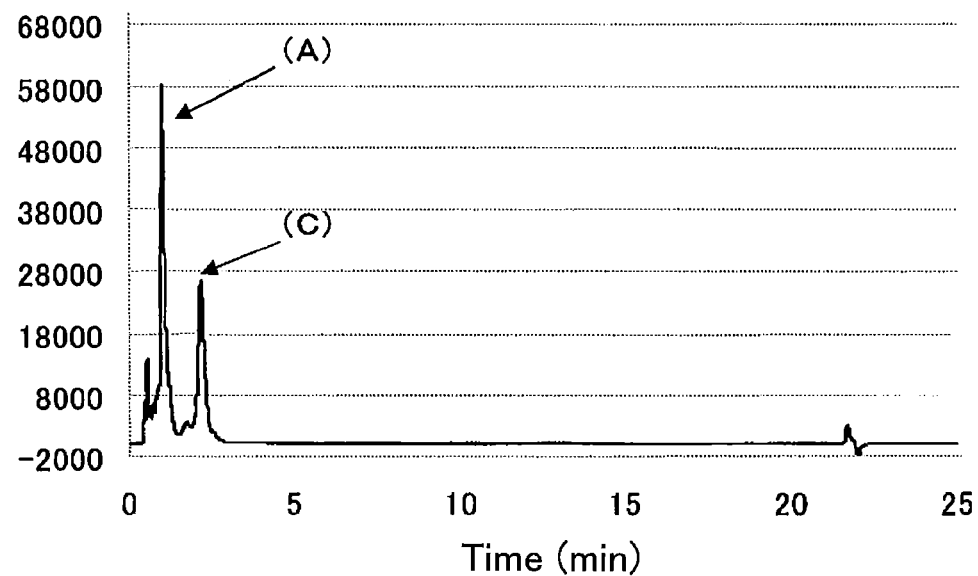

The samples were measured in the same manner as in Example 2, except that eluent 22 (20 mmol/L phosphate buffer (pH 5.4) containing 30 mmol/L sodium perchlorate, 25 mmol/L sodium nitrite, and 25 mmol/L sodium azide) was used as the first eluent, and eluent 23 (40 mmol/L phosphate buffer (pH 8.0) containing 0.8% by weight Triton X-100, 300 mmol/L sodium perchlorate, 25 mmol/L sodium nitrite, and 25 mmol/L sodium azide) was used as the second eluent. FIG. 13 are the resulting chromatograms.

EXAMPLE 10

A sample was prepared by dissolving glycohemoglobin control level II (Sysmex Corp.) in water for injection (200 μL), and further diluting the solution 100-fold with a sample pre-treatment solution (10 mmol/L phosphate buffer (pH 7.0) containing 0.1% by weight Triton X-100).

Another sample was prepared by diluting a hemoglobin S-containing blood sample 100-fold with the sample pre-treatment solution (10 mmol/L phosphate buffer (pH 7.0) containing 0.1% by weight Triton X-100).

Figure 14:
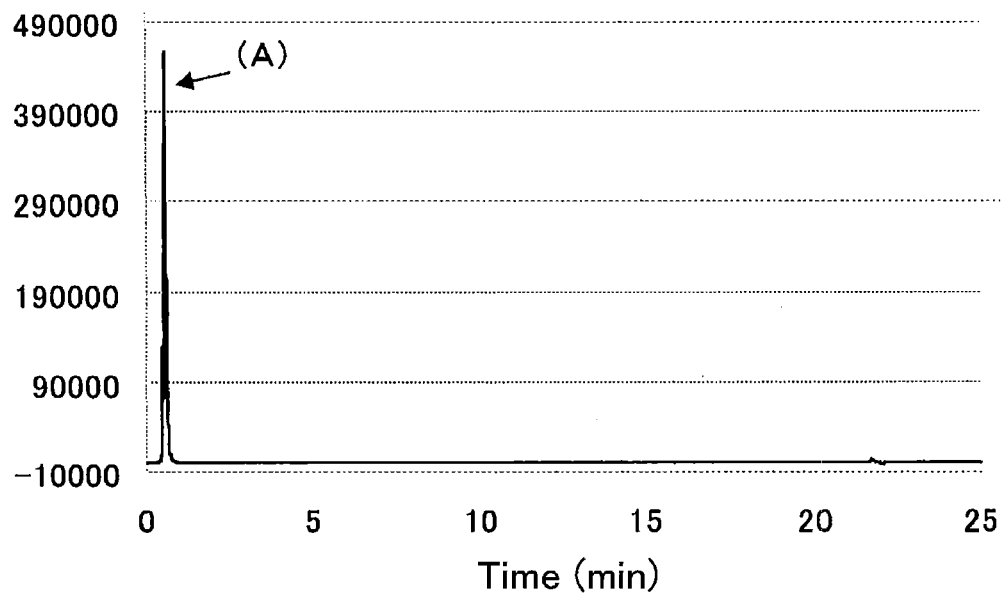
FIGS. 14(a) and 14(b) are chromatograms respectively obtained by measurement of a sample containing glycohemoglobin control level II and a sample containing hemoglobin S-containing blood in Example 10.
Figure 14:
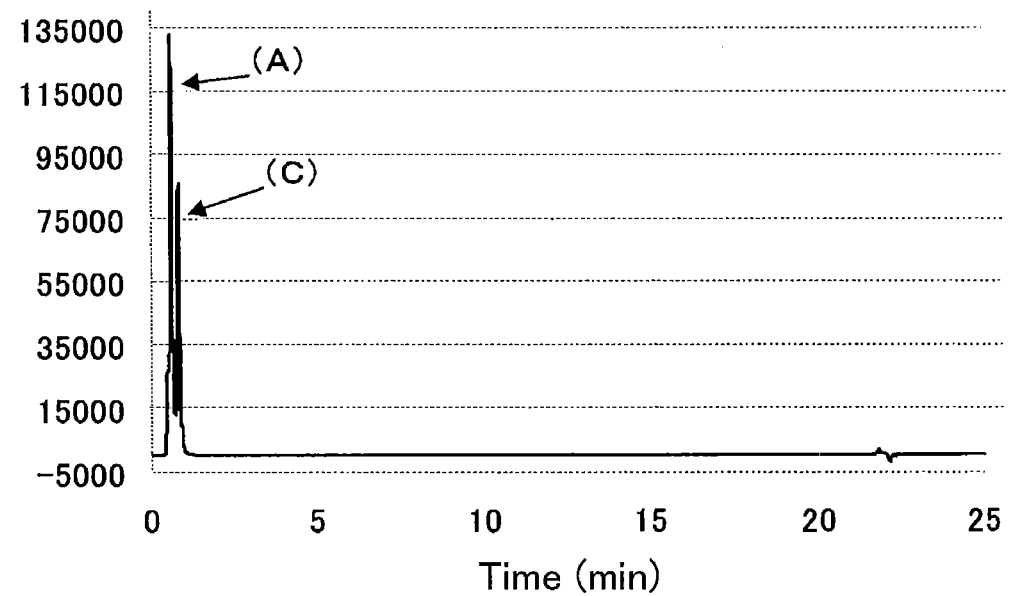

The samples were measured in the same manner as in Example 2, except that eluent 24 (20 mmol/L phosphate buffer (pH 5.4) containing 30 mmol/L sodium perchlorate, 50 mmol/L sodium nitrite, and 50 mmol/L sodium azide) was used as the first eluent, and eluent 25 (40 mmol/L phosphate buffer (pH 8.0) containing 0.8% by weight Triton X-100, 300 mmol/L sodium perchlorate, 50 mmol/L sodium nitrite, and 50 mmol/L sodium azide) was used as the second eluent. FIG. 14 are the resulting chromatograms.

The compositions of the sample pre-treatment solutions and the eluents used for measurement in Examples 2 to 10 and Comparative Examples 2 to 4 are shown in Tables 2 and 3. Table 4 shows how peaks of hemoglobins were separated in the obtained chromatograms as well as the peak patterns of the chromatograms.

In FIGS. 3 to 14, peak (A) corresponds to hemoglobin A0, peak (B) corresponds to hemoglobin A2, and peak (C) corresponds to hemoglobin S.

As seen in FIGS. 3 to 7 (Examples 2 to 6), peak (A) and peak (C) were respectively resolved into sharp single peaks. The quantification accuracy of the chromatogram of FIG. 8 (Example 7) was slightly bad due to small drift but was still at a satisfactory level for identification of the peaks. On the other hand, peak (A) and peak (C) in FIG. 9 (Example 8) were slightly split into tri- or bimodal distributions but were not problematic.

As seen in FIGS. 3 to 9 (Examples 2 to 8), peak (B) was resolved well from peak (A). In contrast, in FIG. 10 (Comparative Example 2), peak (B) of the sample containing glycohemoglobin control level II was not resolved from peak (A) at all, and peak (B) of the hemoglobin S-containing sample was observed as a small shoulder downstream of peak (A). Analysis of other hemoglobins is presumed to result in the same patterns. Thus, the present invention is likely to accurately separate a peak next to that of a hemoglobin species which is present at a high concentration.

In FIGS. 11 and 12 (Comparative Examples 3 and 4), peaks presumed to be decomposed products of the hemoglobins were detected in addition to peaks of the hemoglobins transformed into the met-forms by sodium nitrite or potassium ferricyanide.

In FIGS. 13 and 14 (Examples 9 and 10), the components were respectively resolved into single peaks due to the coexistence of sodium nitrite and sodium azide but eluted at too short elution times due to excessive amounts of sodium nitrite and sodium azide. However, since the single peaks were obtained, the quantification accuracy can be ensured by adjusting other factors such as the buffer agent concentration.

TABLE 2

| | | pH | Phosphate buffer concentration (mmol/L) | Sodium perchlorate concentration (mmol/L) | Oxidant Agent | Oxidant Concentration (mmol/L) | Binder for heme trivalent iron Agent | Binder for heme trivalent iron Concentration (mmol/L) |
|---|---|---|---|---|---|---|---|---|
| Example 2 | Sample pre-treatment solution | 7.0 | 10 | 0 | None | — | None | — |
| | First eluent | 5.4 | 20 | 30 | Sodium nitrite | 1 | Sodium azide | 1 |
| | Second eluent | 8.0 | 40 | 300 | Sodium nitrite | 1 | Sodium azide | 1 |
| Example 3 | Sample pre-treatment solution | 7.0 | 10 | 0 | Sodium nitrite | 1 | Sodium azide | 1 |
| | First eluent | 5.4 | 20 | 30 | Sodium nitrite | 1 | Sodium azide | 1 |
| | Second eluent | 8.0 | 40 | 300 | None | — | Sodium azide | 1 |
| Example 4 | Sample pre-treatment solution | 7.0 | 10 | 0 | None | — | None | — |
| | First eluent | 5.4 | 20 | 30 | Sodium nitrite | 10 | Sodium azide | 1 |
| | Second eluent | 8.0 | 40 | 300 | Sodium nitrite | 10 | Sodium azide | 1 |
| Example 5 | Sample pre-treatment solution | 7.0 | 10 | 0 | None | — | None | — |
| | First eluent | 5.4 | 20 | 30 | Sodium nitrite | 1 | Sodium azide | 10 |
| | Second eluent | 8.0 | 40 | 300 | Sodium nitrite | 1 | Sodium azide | 10 |
| Example 6 | Sample pre-treatment solution | 7.0 | 10 | 0 | None | — | None | — |
| | First eluent | 5.4 | 20 | 30 | Sodium nitrite | 10 | Sodium azide | 10 |
| | Second eluent | 8.0 | 40 | 300 | Sodium nitrite | 10 | Sodium azide | 10 |
| Example 7 | Sample pre-treatment solution | 7.0 | 10 | 0 | Potassium ferricyanide | 1 | Sodium azide | 1 |
| | First eluent | 5.4 | 20 | 30 | Potassium ferricyanide | 1 | Sodium azide | 1 |
| | Second eluent | 8.0 | 40 | 300 | Potassium ferricyanide | 1 | Sodium azide | 1 |
| Example 8 | Sample pre-treatment solution | 7.0 | 10 | 0 | None | — | Sodium azide | 1 |
| | First eluent | 5.4 | 20 | 30 | Sodium ferricyanide | 1 | Sodium azide | 1 |
| | Second eluent | 8.0 | 40 | 300 | None | — | Sodium azide | 1 |
| Example 9 | Sample pre-treatment solution | 7.0 | 10 | 0 | None | — | None | — |
| | First eluent | 5.4 | 20 | 30 | Sodium nitrite | 25 | Sodium azide | 25 |
| | Second eluent | 8.0 | 40 | 300 | Sodium nitrite | 25 | Sodium azide | 25 |

TABLE 2-continued

| | | pH | Phosphate buffer concentration (mmol/L) | Sodium perchlorate concentration (mmol/L) | Oxidant Agent | Concentration (mmol/L) | Binder for heme trivalent iron Agent | Concentration (mmol/L) |
|---|---|---|---|---|---|---|---|---|
| Example 10 | Sample pre-treatment solution | 7.0 | 10 | 0 | None | — | None | — |
| | First eluent | 5.4 | 20 | 30 | Sodium nitrite | 50 | Sodium azide | 50 |
| | Second eluent | 8.0 | 40 | 300 | Sodium nitrite | 50 | Sodium azide | 50 |

TABLE 3

| | | pH | Phosphate buffer concentration (mmol/L) | Sodium perchlorate concentration (mmol/L) | Oxidant Agent | Concentration (mmol/L) | Binder for heme trivalent iron Agent | Concentration (mmol/L) |
|---|---|---|---|---|---|---|---|---|
| Comparative Example 2 | Sample pre-treatment solution | 7.0 | 10 | 0 | None | — | Sodium azide | 1 |
| | First eluent | 5.4 | 20 | 30 | None | — | Sodium azide | 1 |
| | Second eluent | 8.0 | 40 | 300 | None | — | Sodium azide | 1 |
| Comparative Example 3 | Sample pre-treatment solution | 7.0 | 10 | 0 | Sodium nitrite | 1 | None | — |
| | First eluent | 5.4 | 20 | 30 | Sodium nitrite | 1 | None | — |
| | Second eluent | 8.0 | 40 | 300 | Sodium nitrite | 1 | None | — |
| Comparative Example 4 | Sample pre-treatment solution | 7.0 | 10 | 0 | None | — | None | — |
| | First eluent | 5.4 | 20 | 30 | Potassium ferricyanide | 1 | None | — |
| | Second eluent | 8.0 | 40 | 300 | Sodium nitrite | — | None | — |

TABLE 4

| | Separation | Peak pattern Peak (A) | Peak (B) | Peak (C) |
|---|---|---|---|---|
| Example 2 | Separated well | Single peak | Single peak | Single peak |
| Example 3 | Separated well | Single peak | Single peak | Single peak |
| Example 4 | Separated well | Single peak | Single peak | Single peak |
| Example 5 | Separated well | Single peak | Single peak | Single peak |
| Example 6 | Separated well | Single peak | Single peak | Single peak |
| Example 7 | Slight drift | Single peak | Single peak | Single peak |
| Example 8 | Slight drift | Single peak | Single peak | Single peak |
| Example 9 | Peak compression due to high eluting strength | Poorly separated | Not separated | Single peak |
| Example 10 | Peak compression due to high eluting strength | Poorly separated | Not separated | Poorly separated |
| Comparative Example 2 | Poorly separated | Borad | Not separated | Broad |
| Comparative Example 3 | Not separated | Poorly separated | Not separated | Poorly separated |
| Comparative Example 4 | Not separated | Poorly separated | Not separated | Poorly separated |

INDUSTRIAL APPLICABILITY

The present invention provides a method for analyzing hemoglobins which can accurately separate hemoglobins in a short time by liquid chromatography.

The invention claimed is:

1. A method for analyzing hemoglobin S or both of hemoglobin A0 and hemoglobin S in a sample, comprising pre-treating a sample containing hemoglobins with an oxidant and a binder for trivalent heme iron by mixing the oxidant and the binder for trivalent heme iron with a sample pre-treatment solution and/or an eluent and combining the sample with the sample pre-treatment solution and/or the eluent, wherein the concentration of the oxidant in the sample pre-treatment solution or the eluent is 0.05 to 10 mmol/L and the concentration of the binder for trivalent heme iron in the sample pre-treatment solution or the eluent is 0.05 to 10 mmol/L, subjecting the sample to ion-exchange liquid chromatography and identifying peaks on a resulting chromatogram that correspond to hemoglobin S or both hemoglobin A0 and hemoglobin S.

2. The method for analyzing hemoglobin S or both of hemoglobin A0 and hemoglobin S in a sample according to claim 1,
wherein the oxidant is a substance capable of transforming hemoglobins to their met-forms.

3. The method for analyzing hemoglobin S or both of hemoglobin A0 and hemoglobin S in a sample according to claim 2,
wherein the oxidant is a nitrite salt.

4. The method for analyzing hemoglobin S or both of hemoglobin A0 and hemoglobin S in a sample according to claim 3,
wherein the oxidant is sodium nitrite.

5. The method for analyzing hemoglobin S or both of hemoglobin A0 and hemoglobin S in a sample according to claim 1,
wherein the binder for trivalent heme iron is a substance that binds to trivalent iron in methemoglobin.

6. The method for analyzing hemoglobin S or both of hemoglobin A0 and hemoglobin S in a sample according to claim 5,
wherein the binder for trivalent heme iron is an azide.

7. The method for analyzing hemoglobin S or both of hemoglobin A0 and hemoglobin S in a sample according to claim 6,
wherein the binder for trivalent heme iron is sodium azide.

* * * * *